United States Patent
Chartrand et al.

(10) Patent No.: US 10,710,116 B2
(45) Date of Patent: Jul. 14, 2020

(54) METHODS AND SYSTEMS FOR MANUFACTURING AN ULTRASOUND PROBE

(71) Applicant: General Electric Company, Schenectady, NY (US)

(72) Inventors: David A. Chartrand, Phoenix, AZ (US); Reinhold Bruestle, Zipf (AT)

(73) Assignee: General Electric Company, Schenectady, NY (US)

(*) Notice: Subject to any disclaimer, the term of this patent is extended or adjusted under 35 U.S.C. 154(b) by 341 days.

(21) Appl. No.: 15/711,464

(22) Filed: Sep. 21, 2017

(65) Prior Publication Data

US 2019/0084004 A1 Mar. 21, 2019

(51) Int. Cl.
*B06B 1/06* (2006.01)
*A61B 8/00* (2006.01)
*H01L 41/25* (2013.01)

(52) U.S. Cl.
CPC ............ *B06B 1/0622* (2013.01); *A61B 8/445* (2013.01); *A61B 8/4466* (2013.01); *B06B 1/067* (2013.01); *H01L 41/25* (2013.01); *A61B 8/4483* (2013.01)

(58) Field of Classification Search
CPC combination set(s) only.
See application file for complete search history.

(56) References Cited

U.S. PATENT DOCUMENTS

| | | | |
|---|---|---|---|
| 9,539,667 B2 | 1/2017 | Bruestle et al. | |
| 2010/0066207 A1* | 3/2010 | Saito ................... | A61B 8/4281 310/335 |
| 2012/0183793 A1 | 7/2012 | Wolfgang et al. | |
| 2013/0018266 A1* | 1/2013 | Nishikubo ........... | A61B 8/4483 600/443 |
| 2013/0315035 A1* | 11/2013 | Tai ........................ | B06B 1/0622 367/140 |
| 2014/0221841 A1* | 8/2014 | Okuda .................. | B06B 1/0677 600/459 |
| 2014/0249419 A1* | 9/2014 | Morita .................. | G10K 11/02 600/459 |
| 2015/0018266 A1* | 1/2015 | Hodge .................. | C07H 15/04 510/470 |
| 2015/0045671 A1* | 2/2015 | Ozawa ................. | A61B 8/4444 600/459 |

* cited by examiner

*Primary Examiner* — Bryan P Gordon
(74) *Attorney, Agent, or Firm* — The Small Patent Law Group LLC; Dean D. Small (57) ABSTRACT

Systems and methods described herein generally relate to forming a conductive layer of an ultrasound probe. The systems and methods form an ultrasound probe that includes a piezoelectric layer, and first and second matching layers. The first matching layer is interposed between the second matching layer and the piezoelectric layer. The second matching layer formed from a material having a select acoustic impedance from a laser activated molded interconnect device (MID) or a three-dimensional printer. The second matching layer being electrically coupled to the piezoelectric layer.

11 Claims, 5 Drawing Sheets

METHODS AND SYSTEMS FOR MANUFACTURING AN ULTRASOUND PROBE

FIELD

Embodiments described herein generally relate to forming a conductive layer of an ultrasound probe.

BACKGROUND OF THE INVENTION

Conventional ultrasound probes include a series of matching layers. The matching layers are configured to adjust acoustic impedance characteristics of a piezoelectric layer, by decreasing acoustic waves within the ultrasound probe to match the patient. The matching layers include one or more conductive layers. For example, the conductive layers are configured as a ground return for the matching layers of the ultrasound probe to an electrical ground.

However, the conventional methods to form the conductive layers are cost prohibitive. For example, a plastic material (e.g., Rexolite, Acrylonitrile Butadiene Styrene) is machined to a specified shape. A metalized surface is formed on a surface of the plastic material. The metalized surface is formed using a vapor deposition process. The vapor deposition process is initiated using a seed layer of gold. Additional gold is applied, using a sputter process, to produce a thickness of the gold to a required level. The rate of growth of the thickness is slow due to the slow deposition rate within the sputter chamber, which further increases costs.

BRIEF DESCRIPTION OF THE INVENTION

In an embodiment a method (e.g., for manufacturing a second matching layer) is provided. The method includes forming a second matching layer of an ultrasound probe from a material having a select acoustic impedance. The method includes activating a bottom surface area of the second matching layer using a laser beam based on a template to form a conductive layer, and electrically coupling the conductive layer to a piezoelectric layer.

In an embodiment a method (e.g., for manufacturing a first matching layer) is provided. The method includes receiving a template for a second matching layer, and using a three-dimensional (3D) printer to form the second matching layer of an ultrasound probe based on the template. The second matching layer having a conductive material with a select acoustic impedance. The method includes electrically coupling the second matching layer to a piezoelectric layer.

In an embodiment, an ultrasound probe is provided. The probe includes a piezoelectric layer, and first and second matching layers. The first matching layer is interposed between the second matching layer and the piezoelectric layer. The second matching layer formed from a material having a select acoustic impedance from a laser activated molded interconnect device (MID) or a three-dimensional printer. The second matching layer being electrically coupled to the piezoelectric layer.

DETAILED DESCRIPTION OF THE INVENTION

The following detailed description of certain embodiments will be better understood when read in conjunction with the appended drawings. To the extent that the figures illustrate diagrams of the functional modules of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like). Similarly, the programs may be stand-alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Various embodiments described herein generally relate to manufacturing a conductive layer at a matching layer of a ultrasound probe. The conductive layer is interposed between first and second matching layers of the ultrasound probe. The matching layers are configured to reduce the acoustic impedance difference between the piezoelectric layer and the patient. The matching layer includes a conductive layer positioned along a backside of the second matching layer. The conductive layer is configured to electrically couple the second matching layer to a electrodes of a flex. The matching layers are formed utilizing a laser activated molded interconnect device (MID) and/or a three-dimensional (3D) printer.

A technical effect of at least one embodiment described herein eliminates the use of high cost vapor deposition process to form the conductive layer. A technical effect of at least one embodiment described herein improves yield fallout seen from current metalized matching layers where metallization adhesion variation results in partial delamination during element dicing.

Figure 1:
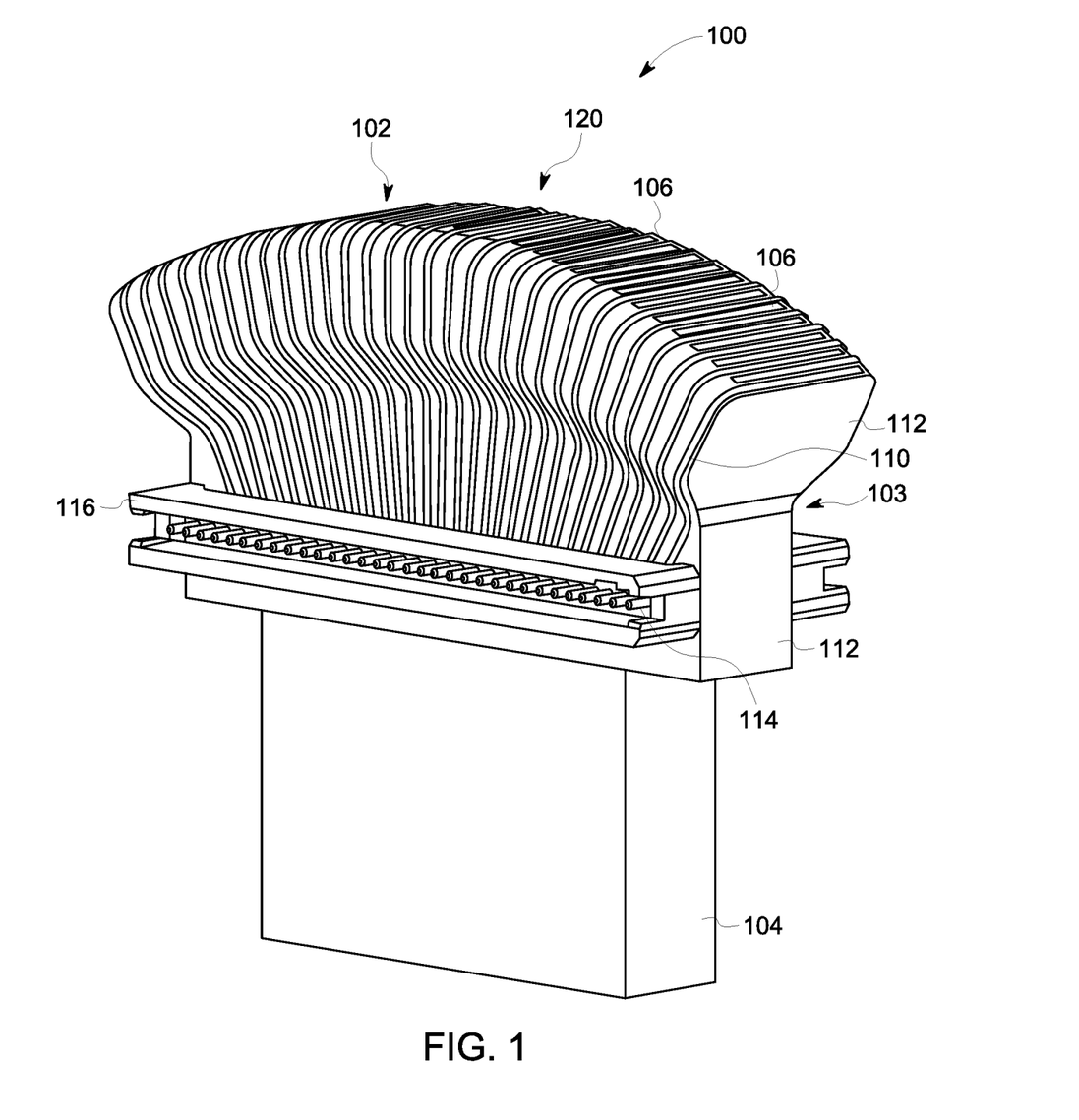
FIG. 1 illustrates an embodiment of a perspective view of an ultrasound probe.

FIG. 1 illustrates an embodiment of a perspective view of an ultrasound probe 100. Additionally or alternatively, embodiments of the ultrasound probe 100 is described in U.S. Pat. No. 9,539,667, entitled, "SYSTEMS AND METHODS FOR CONNECTION TO A TRANSDUCER IN ULTRASOUND PROBES," which is incorporated by reference in its entirety.

The probe 100 includes a scanning end 102, having an integrated support and electrical connection member illustrated as a molded interconnect device (MID) 103. The probe 100 may be an ultrasound imaging probe having a non-mechanically moving (e.g., electronically steerable) or mechanically moving scan head, which includes a transducer carrier (provided by the MID 103) for supporting a transducer array 120 (which in various embodiments may be formed from piezoelectric ceramic elements, matching layers, and/or acoustic stack laminated thereon). However, it should be noted that various embodiments may be implemented in different types of probes having different designs and are not limited to the probes illustrated and described herein.

The transducer array 120 in various embodiments may be formed from any suitable components, for example, a piezoelectric ceramic, which is supported on the MID 103. The probe 100 includes electrical interconnects 106 integrated with the MID 103 for communicating with and electrically controlling the transducer array 120. A pair of connectors 110 are also coupled to the MID 103 to allow connection to the electrical interconnects 106. The electrical interconnects 106 are applied to or formed on a base 112, such as a plastic base. In various embodiments, a single interface and support element, such as the MID 103, is provided having the electrical interconnects 106 and support portion for the transducer array 120 combined or integrated into a single physical structure or part. Additionally or alternatively, the MID 103 provides the functionality and/or operation of a support structure and electrical interconnect (instead of, for example, a separate carrier and scan head flex PCB). The MID 103 in various embodiments supports and provides interconnection to the transducer array 120 within the probe 100.

A pair of connectors 116 are also coupled to the MID 103 to allow connection to the electrical interconnects 106, such as for connection to a system cable. It should be noted that although two connectors 116 are shown, fewer or additional connectors 116 may be provided and coupled to the same or different portions of the MID 103. The connectors 116 may be any suitable type of connection interface, which in one embodiment is a board-to-board connector 114, such as for cable interconnect and includes a plurality of connector elements.

Optionally, an additional portion 104 may be provided that extends from the base 112, which may be coupled thereto or form part of the base 112. In various embodiments, the portion 104 allows for connection of the MID 103 of the probe 100, such as mounting of the MID 103 to and within the housing of the probe 100.

Figure 2:
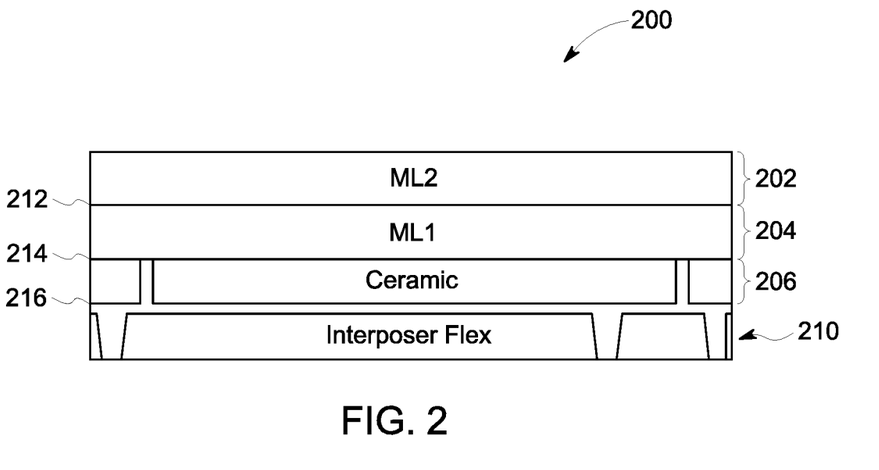
FIG. 2 illustrates an embodiment of an acoustic stack of an ultrasound probe.

FIG. 2 illustrates an embodiment of an acoustic stack 200, such as for the ultrasound probe 100. The acoustic stack 200 includes one or more matching layers 202, 204 and a piezoelectric layer 206. The piezoelectric layer 206 represents an electrically conductive structure, such as ceramic. The acoustic stack 200 is shown having a second matching layer 202 and a first matching layer 204. The second matching layer 202 is interposed between the first matching layer 204 and a lens (not shown). The lens is positioned adjacent to the patient (e.g., skin). The first matching layer 204 is interposed between the second matching layer 204 and the piezoelectric layer 206. The matching layers 202, 204 have acoustic impedance characteristics, which are configured to reduce the acoustic impedance of the piezoelectric layer 206 emitted by the ultrasound probe 100. For example, the materials of the first and second matching layers 202, 204 are configured to have select acoustic impedances. The first matching layer 204 is configured to reduce the acoustic impedance characteristics of the piezoelectric layer 206 at the select acoustic impedance at a range of 2-3 Megarayles. In another example, the second matching layer 202 is configured to reduce the acoustic impedance characteristics of the first matching layer 204 at the select acoustic impedance at a range of 6-15 Megarayles. Optionally, the acoustic stack 200 includes dematching layer (not shown) interposed between the piezoelectric layer 206 and a flex 210. Additionally or alternatively, the acoustic stack 200 does not include the dematching layer, rather the flex 210 (as shown in FIG. 2) is positioned adjacent to the piezoelectric layer 206. The flex 210 is configured to electrically couple the ultrasound probe to an ultrasound imaging system.

The matching layers 202, 204 and the piezoelectric layer 206 (e.g., the ceramic) include conductive layers 212, 214, 216 that electrically couple the piezoelectric layer 206 to electrodes (not shown) on the flex 210. The electrodes are positioned a long a surface of the flex and/or positioned within the flex. The conductive layers 214, 216 are positioned on opposing sides of the piezoelectric layer 206. The conductive layer 212 is electrically coupled to an electrically conductive portion of the first matching layer 204. The electrically conductive portion electrically couples the conductive layers 212, 214, which enables the conductive layer 212 to be electrically coupled to the electrodes of the flex 210. For example, the conductive layer 212 enables the matching layer 202 to electrically couple the electrodes of the flex 210 via the electrically conductive portion of the matching layer 204 and the piezoelectric layer 206 (e.g., ceramic).

Figure 3:
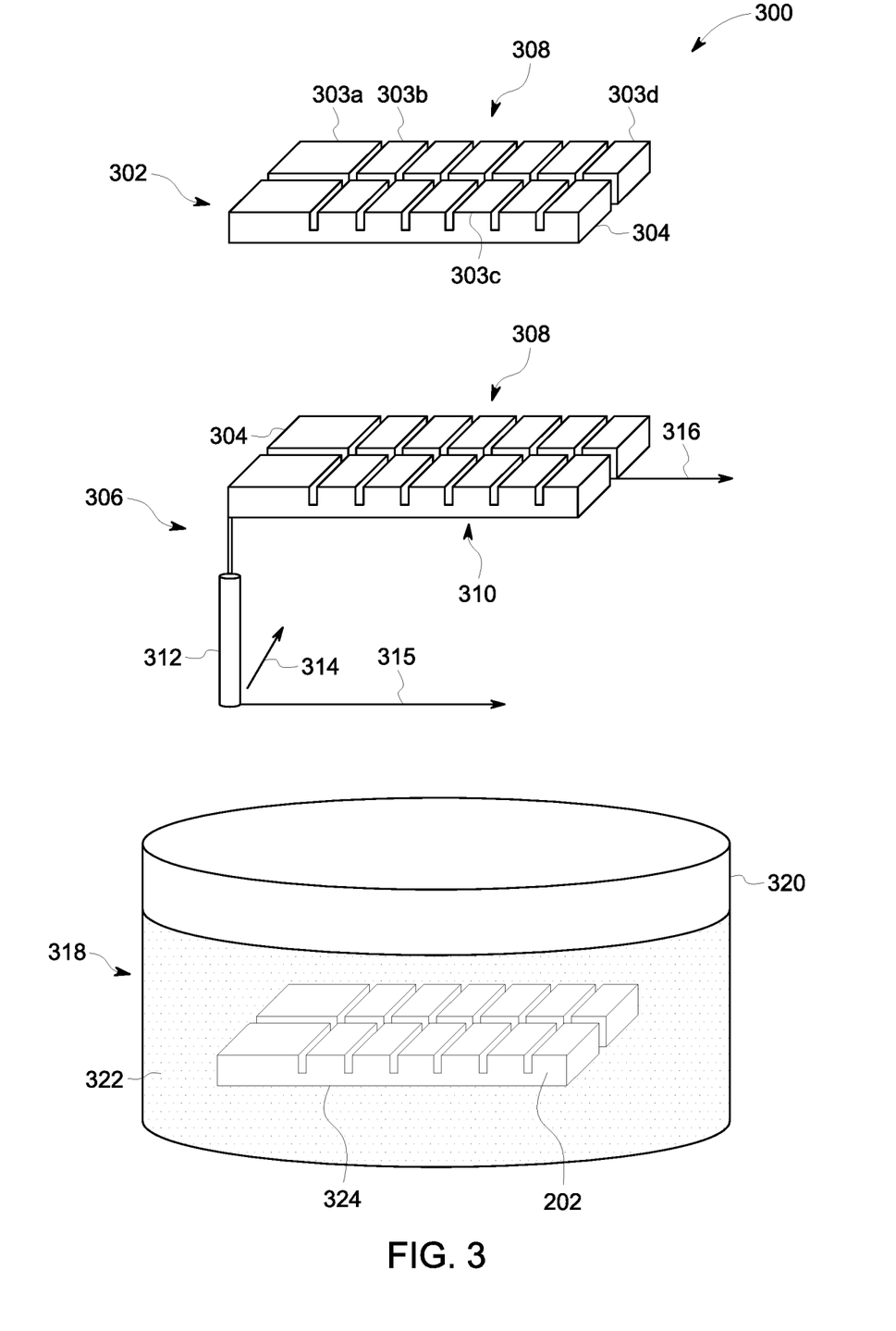
FIG. 3 illustrates an embodiment of a process for laser activated molded interconnect devices to form a second matching layer.

FIG. 3 illustrates an embodiment of a process 300 for the laser activated MID to form a second matching layer. The process 300 illustrates forming the conductive layer 212 utilizing the laser activated molded interconnect device (MID).

At 302, a second matching layer is formed using an injection molding, such as a single-component injection molding. The injection molding is configured to produce a form factor and/or shape of a second matching layer 304. The second matching layer 304 may include an array of transducer elements 303*a-d* arranged as a matrix array. For example, the transducer elements 303*a-d* are shown as columns along a top surface area 308 of the second matching layer 304. A material of the first matching layer is configured to reduce an acoustic impedance at a select acoustic impedance (e.g., 10-15 Megarayles). A material of the second matching layer 304 may include at least one of Acrylonitrile butadiene styrene (ABS), polycarbonate (PC), Polymerization (PA), Polyphthalamide (PPA), Polybutylene terephthalate (PBT), Cyclic Olefin Copolymer (COP), Polyphenyl Ether (PPE), Liquid-crystal polymer (LCP), Polyethylenimine (PEI), Polyether ether ketone (PEEK), Polyphenylene sulfide (PPS), and/or the like.

Additionally or alternatively, an additive may be included along an outer surface of the material from the forming process. For example, a coating is applied to the outer surface of the material to encapsulate with an organic coating. The additive can be a metallic particulate encapsulated with an organic coating, which does not alter the proprieties of the material of the second matching layer 304.

At 306, the bottom surface area 310 of the second matching layer 304 is activated using heat, such as from a laser beam 312. For example, the laser beam 312 activates the additive (e.g., the organic coating) along the bottom surface area 310 of the second matching layer 304. The laser beam 312 is operably coupled to a pair of actuators (e.g., electric motors), which enables the laser beam 312 to traverse along directions 314-315. The laser beam 312 activates the organic coating along the bottom surface area 310 by heating the entire bottom surface area 310 of the second matching layer 304.

The heat of the laser beam 312 generates a physical-chemical reaction on the bottom surface area 310 of the second matching layer 304. For example, the laser beam 312 breaks down the organic coating of the additive to expose the metallic particles. Additionally or alternatively, the laser beam 312 forms a rough surface and/or cavities (e.g., 324) on the bottom surface area 310 of the second matching layer 304. For example, the activated additives catalysis the area to increase adhesion for the metallization process.

At 318, the second matching layer 304 is submerged into a container 320. The container 320 holds a chemical compound 322 that induces metal to form at the positions activated by the laser beam 312, such as at cavities 324. For example, the chemical compound 322 may be a chemical electrolyte that includes at least one of copper, nickel, gold, iron, magnesium, aluminum, lithium, and/or the like. When the chemical electrolyte is in contact with the cavities 324 formed by the laser beam 312, an electronegative potential is deposited from the chemical compound 322 onto the cavities 324. The electronegative potential attracts additional metal within the chemical compound 322, which thickens the metal layer over time to form the conductive layer 212 (FIG. 2) and the second matching layer 202.

Additionally or alternatively, the chemical compound 322 may be adjusted overtime to a predefined sequence. The predefined sequence adjusts the metal content of the chemical compound 322 over time. For example only, the sequence may alternate between different metals of the chemical electrolytes such that the conductive layer 212 includes different metal layers.

Additionally or alternatively, the laser beam 312 may activate alternative surface areas of the second matching layer 304. For example, the laser beam 312 may activate the top surface area 308 of the second matching layer 304. Based on the activation of the second matching layer 304, the top surface area 308 includes a metal layer when submerged in the chemical compound 322. The metal layer provides an electromagnetic shield, which protects the ultrasound probe 100 from electrical noise emitted from alternative electrical systems proximate to the ultrasound probe 100.

Figure 4:
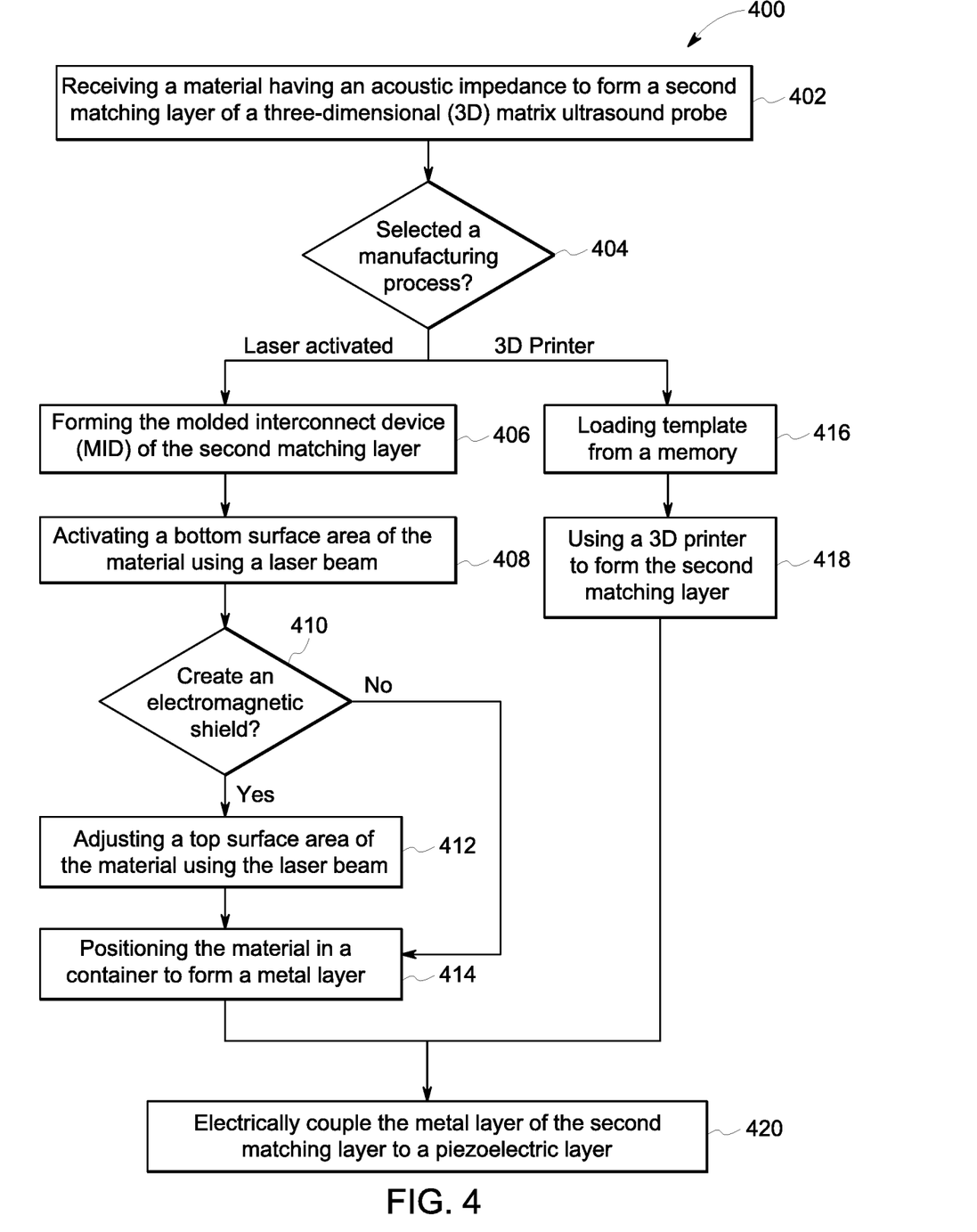
FIG. 4 illustrates an embodiment of a flow chart of a method for manufacturing a second matching layer.

FIG. 4 illustrates an embodiment of a flow chart of a method 400 for manufacturing a first matching layer. The method 400, for example, may employ structures or aspects of various embodiments (e.g., systems and/or methods) discussed herein. In various embodiments, certain steps (or operations) may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion. In various embodiments, portions, aspects, and/or variations of the method 400 may be used as one or more algorithms to direct hardware to perform one or more operations described herein.

Beginning at 402, the controller circuit 502 (FIG. 4) receives a material having an acoustic impedance to form the second matching layer 202 of the ultrasound probe 100. The material is configured to have the select acoustic impedance, which can reduce the impedance characteristics by 2-3 Megarayles of the first matching layer 202. The material is received by a manufacturing system 500.

Figure 5:
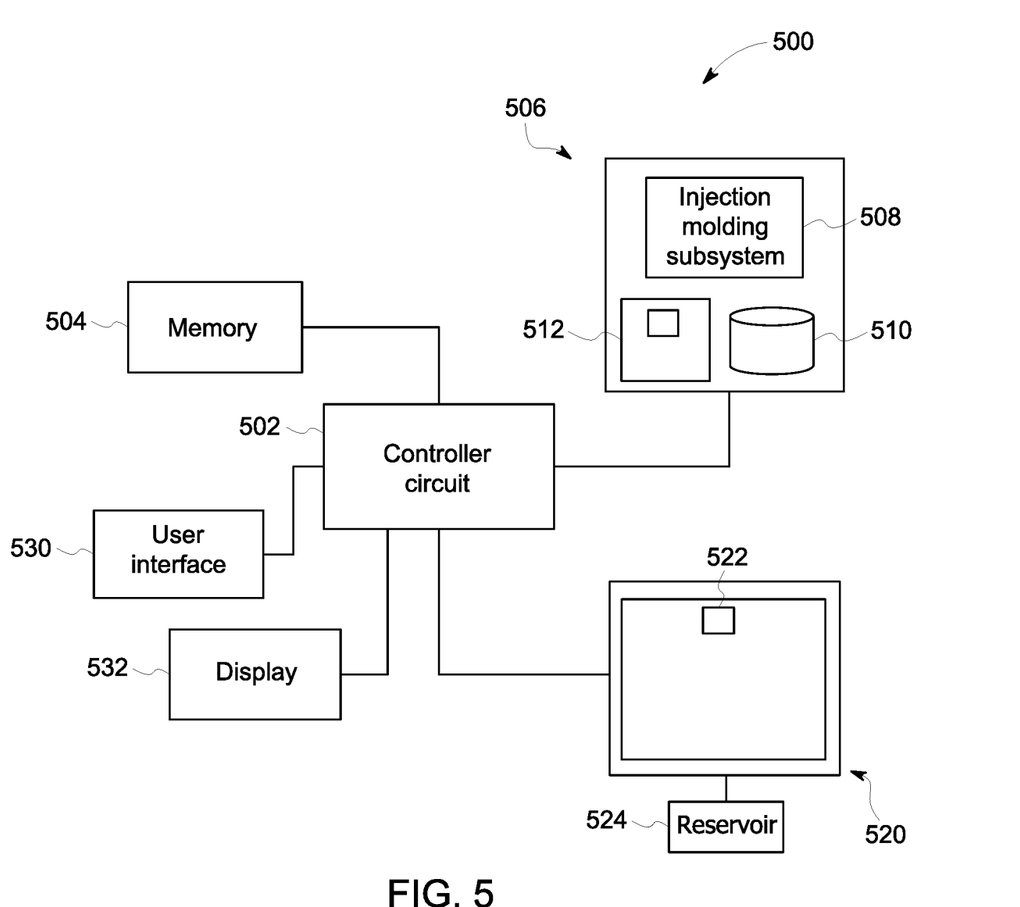
FIG. 5 illustrates an embodiment of a schematic block diagram of a manufacturing system.

FIG. 5 illustrates an embodiment of the manufacturing system 500. The manufacturing system 500 includes a controller circuit 502. The controller circuit 502 is configured to control the operation of the manufacturing system 500. The controller circuit 502 may include one or more processors. Optionally, the controller circuit 502 may include a central processing unit (CPU), one or more microprocessors, a graphics processing unit (GPU), or any other electronic component capable of processing inputted data according to specific logical instructions. Optionally, the controller circuit 502 may include and/or represent one or more hardware circuits or circuitry that include, are connected with, or that both include and are connected with one or more processors, controllers, and/or other hardware logic-based devices. Additionally or alternatively, the controller circuit 502 may execute instructions stored on a tangible and non-transitory computer readable medium (e.g., the memory 504).

The memory 504 includes parameters, templates, algorithms, data values, and/or the like utilized by the controller circuit 502 to perform one or more operations described herein. The memory 504 may be a tangible and non-transitory computer readable medium such as flash memory, RAM, ROM, EEPROM, and/or the like.

The controller circuit 502 is operably coupled to the display 532 and the user interface 530. The display 532 may include one or more liquid crystal displays (e.g., light emitting diode (LED) backlight), organic light emitting diode (OLED) displays, plasma displays, CRT displays, and/or the like. The display 532 may display a status of the manufacturing process of the second matching layer 202.

The user interface 530 controls operations of the controller circuit 502 and the manufacturing system 500. The user interface 530 is configured to receive inputs from the user and/or operator of the manufacturing system 500. The user interface 530 may include a keyboard, a mouse, a touchpad, one or more physical buttons, and/or the like. Optionally, the display 532 may be a touch screen display, which includes at least a portion of the user interface 530.

The controller circuit 502 is operably coupled to a laser activated MID 506 and a 3D printer 520. The controller circuit 502 may receive the material at reservoirs for the laser activated MID 506 and the 3D printer 520. Optionally, the operations performed by the laser activated MID 506 and/or the 3D printer 520 may be integrated with and/or performed by the controller circuit 502.

For example, the laser activated MID 506 includes an injection molding subsystem 508. The injection molding subsystem 508 includes a mold and/or die, which forms the second matching layer 304 (FIG. 3). The mold and/or die represents a shape and/or size of the second matching layer 304. For example, the mold and/or die may include transducer elements (e.g., the transducer elements 303a-d shown in FIG. 3) to form the matrix array. The injection molding subsystem 508 is operably coupled to a reservoir (not shown) which includes the material. For example, the material for the laser activated MID 506 may include Acrylonitrile butadiene styrene (ABS), polycarbonate (PC), Polymerization (PA), Polyphthalamide (PPA), Polybutylene terephthalate (PBT), Cyclic Olefin Copolymer (COP), Polyphenyl Ether (PPE), Liquid-crystal polymer (LCP), Polyethylenimine (PEI), Polyether ether ketone (PEEK), or Polyphenylene sulfide (PPS), and/or the like. The controller circuit 502 may detect when the material is received at the reservoir of the injection molding subsystem 508.

The laser activated MID 506 includes an enclosure 512 and a container 510. The enclosure 512 includes a laser beam (e.g., the laser beam 312 of FIG. 3) for activating surface areas of the second matching layer 202 generated by the injection molding subsystem. For example, the enclosure 512 include a set of actuators (e.g., electrical motors) which are configured to adjust a position of the laser beam 312, a position of the second matching layer 202, and/or the like. The laser beam 312 forms cavities on a surface of the second matching layer 202. The laser activated MID 506 includes a container 510 that is filled from a reservoir with a chemical compound that induces metal to form on surface of the second matching layer 202.

The 3D printer 520 may represent an electron-beam freeform and/or additive fabrication, an inkjet head 3D printer, a direct ink writing 3D printer, and/or the like. The 3D printer 520 is operably coupled to a reservoir 524. The reservoir may include a conductive metal for constructing the second matching layer 202. For example, the second matching layer 202 constructed by the 3D printer 520 includes a conductive layer 212 which extends throughout the second matching layer 202. The 3D printer 520 forms the second matching layer 202 from the conductive material. The conductive material for the 3D printer 520 may include at least one of copper, nickel, gold, iron, magnesium, aluminum, lithium, and/or the like. The controller circuit 502 may detect when the material is received at the reservoir 524.

At 404, the controller circuit 502 selects the manufacturing process to form the second matching layer 202. The manufacturing process can represent the laser activated MID 506 and/or the 3D printer 520. For example, the controller circuit 502 may receive a selection from the user interface 530 indicative and/or representing a selection of the manufacturing process. Additionally or alternatively, the controller circuit 502 may automatically select one of the manufacturing processes based on an identification by the controller circuit 502 on which of the detected laser activated MID 506 and/or the 3D printer 520 receives the material.

If the controller circuit 502 receive a selection that the laser activated MID 506 is selected, then at 406, the controller circuit 502 forms the second matching layer 202. In connection with FIG. 3, the process 300 begins by forming the second matching layer 304. The controller circuit 502 sends instructions to the injection molding subsystem 508 to receive the material from the reservoir. The material is heated and filled within the injection molding subsystem 508, which forms a shape of the second matching layer 304.

Additionally or alternatively, the second matching layer 304 is coated with a metallic particulate encapsulated with an organic coating. The organic coating breaks down when exposed to heat, such as from the laser beam 312. The break down of the organic coating exposes the metallic particles on a surface of the second matching layer 304.

At 408, the laser activated MID 506 adjusts a bottom surface area 310 of the material using the laser beam 312. The laser beam 312 is operably coupled to an actuator. The actuator is configured to adjust a position of the laser beam 312 along the directions 314-315 with respect to the second matching layer 304. Movement of the laser beam 312 is based on a template stored in the memory 504. For example, the template may include details on positions along one or more surface areas of the second matching layer 304, which is activated by the laser beam 312. The template may include instructions to adjust the bottom surface area 310 of the material of the second matching layer 304. For example, based on the template the laser activated MID 506 instructs the laser beam 312 to expose the bottom surface area 310 with the laser beam 312.

As the laser beam 312 activates the bottom surface area 310, the laser beam 312 activates the additive within the material of the second matching layer 304. The laser beam 312 generates a physical-chemical reaction on the bottom surface area 310 of the second matching layer 304. For example, the laser beam 312 breaks down the organic coating of the additive on the material to expose the metallic particles underneath the organic coating. Additionally or alternatively, the laser beam 312 forms a rough surface and/or cavities on the bottom surface area 310 of the second matching layer 304. The heat from the laser beam 312 activates the additives to increase adhesion for the metallization process.

At 410, the controller circuit 502 determines whether an electromagnetic shield is needed. For example, the controller circuit 502 identifies whether the template includes positioning the laser beam 312 along a top surface area 308 of the second matching layer 304. The controller circuit 502 may identify whether the template includes positions along opposing sides (e.g., the bottom surface area 310, the top surface area 308) of the second matching layer 304.

If the controller circuit 502 determines the electromagnetic shield is needed, then at 412, the laser activated MID 506 adjusts the top surface area 308 of the material using the laser beam 312. For example, the laser activated MID 506 rotates the second matching layer 304. The second matching layer 304 can be operably coupled to an actuator (e.g., electric motor), which rotates the second matching layer 304 about an axis 316. The actuator rotates the second matching layer 304 such that the top surface area 308 is facing the laser beam 312. The controller circuit 502 is positioned such that a position of the laser beam 312 is adjusted along the directions 314-315 with respect to the second matching layer 304. For example, based on the template the controller circuit 502 instructs the laser beam 312 to heat the top surface area 308. As the laser beam 312 heats the top surface area 308, the laser beam 312 activates the additive within the material of the second matching layer 304. For example, the laser beam 312 forms a rough surface and/or cavities on the top surface area 308 of the second matching layer 304.

At 414, the laser activated MID 506 positions the material in the container 510 to form a metal layer. The container 510 holds a chemical compound, such as a chemical electrolyte, that induces metal to form within the cavities. For example, the chemical compound may include at least one of copper, nickel, gold, iron, magnesium, aluminum, lithium, and/or the like. When the chemical electrolyte is in contact with the cavities formed by the laser beam 312, an electronegative potential is deposited from the chemical compound onto the cavities. The electronegative potential attracts additional metal within the chemical compound, which thickens the metal layer over time to form the conductive layer 212 (FIG. 2) and the second matching layer 202.

Additionally or alternatively, the chemical compound may be adjusted according to a predefined sequence stored in the memory 504. The sequence may adjust the metal of the chemical compound based on the predefined sequence. The sequence may form different metal layers within the cavities formed by the chemical compound. For example, the laser activated MID 506 may drain the chemical compound within the container 510, and refill the container 510 with an alternative chemical compound from the reservoir. The laser activated MID 506 may alternate between different chemical electrolytes representing different metal compounds such that the conductive layer 212 is formed by different metal layers.

For example, the laser activated MID 506 fills the container 510 with the chemical compound that includes the metal compound of copper. Overtime, as the copper deposition increases in thickness. After a set period of time and/or thickness, the laser activated MID 506 drains the chemical compound from the container 510, and refills the chemical compound to include an alternative metal compound, such as nickel. For example, copper has poor oxidation resistance, the nickel further protects the copper. Overtime, the nickel deposition increases in thickness. The laser activated MID 506 drains the chemical compound from the container 510 after a set period of time and/or thickness. Optionally, the controller circuit 502 may fill the container 510 with the chemical compound that includes the metal compound of gold, which provides further oxidation resistance.

If the controller circuit 502 receive a selection that the 3D printer 520 is selected, then at 416, the controller circuit 502 loads a template from the memory 504 to the 3D printer 520. The template may represent a file format utilized (e.g., CAD) by the 3D printer 520 to construct the second matching layer 202. For example, the template includes a series of instructions (e.g., shapes, sizes, measurements) used to form the second matching layer 202. The 3D printer 520 executes the template to construct the second matching layer 202.

At 418, using the 3D printer 520 to form the second matching layer 202. The reservoir 524 may include a conductive metal that includes at least one of copper, nickel, gold, iron, magnesium, aluminum, lithium, and/or the like. The conductive metal is configured to have the select acoustic impedance of the second matching layer 202. Optionally, the conductive metal may be in the form of a metal powder and/or a metal wire. The 3D printer 520 forms the second matching layer 202 utilizing a laser 522. For example, the 3D printer 520 forms the second matching layer 202 by melting the metal powder using the heat (e.g., an electron-beam melting) generated by the laser 522. In another example, the 3D printer 520 forms the first matching later 202 by melting the metal wire using the heat generated by the laser 522.

At 420, the controller circuit 502 electrically couples the metal layer (e.g., the conductive layer 212) to the piezoelectric layer 206. For example, the controller circuit 502 positions the second matching layer 202 directly adjacent to the first matching layer 204. Optionally, the first matching layer 204 may be manufactured utilizing the laser activated MID 506 and/or the 3D printer 520. The conductive layer 212 of the second matching layer 202 is electrically coupled to the electrically conductive portion of the first matching layer 204. The electrically conductive portion electrically couples the conductive layer 212 of the second matching layer 202 to the piezoelectric layer 206 and the electrodes of the flex 210.

In an embodiment a method (e.g., for manufacturing a second matching layer) is provided. The method includes forming a second matching layer of an ultrasound probe from a material having a select acoustic impedance. The method includes activating a bottom surface area of the second matching layer using a laser beam based on a template to form a conductive layer, and electrically coupling the conductive layer to a piezoelectric layer.

Optionally, the material includes Acrylonitrile butadiene styrene (ABS), a polycarbonate (PC), Polymerization (PA), Polyphthalamide (PPA), Polybutylene terephthalate (PBT), Cyclic Olefin Copolymer (COP), Polyphenyl Ether (PPE), Liquid-crystal polymer (LCP), Polyethylenimine (PEI), Polyether ether ketone (PEEK), or Polyphenylene sulfide (PPS). Optionally, the method includes coating the material with a metallic particulate encapsulated with an organic coating such that the laser beam is configured to break down the organic coating to expose the metallic particles. Optionally, the method includes positioning the material in a container to form a metal layer on the activated bottom surface area, wherein the container includes a chemical electrolyte that includes a metal compound. Additionally or alternatively, the method includes adjusting the metal compound within the container based on a predetermined sequence, such that the conductive layer includes different metal layers. Optionally, the template includes an electromagnetic shield, and further comprising directing the laser beam to activate a top surface area of the second matching layer. Optionally, the template includes an activation path for the laser beam to follow with respect to the second matching layer.

In an embodiment a method (e.g., for manufacturing a second matching layer) is provided. The method includes receiving a template for a second matching layer, and using a three-dimensional (3D) printer to form a second matching layer of an ultrasound probe based on the template. The second matching layer having a conductive material with a select acoustic impedance. The method includes electrically coupling the second matching layer to a piezoelectric layer.

Optionally, to form the second matching layer the 3D printer heats the conductive material using a laser based on the template. Additionally or alternatively, the conductive material represents a metal powder that is melted by the laser to form the second matching layer. Optionally, the conductive material represents a metal wire that is melted by the laser to form the second matching layer. Additionally or alternatively, the template indicates a shape or size of the second matching layer. Optionally, the conductive material includes at least one of copper, nickel, gold, iron, magnesium, aluminum, or lithium.

In an embodiment, an ultrasound probe is provided. The probe includes a piezoelectric layer, and first and second matching layers. The first matching layer is interposed between the second matching layer and the piezoelectric layer. The second matching layer formed from a material having a select acoustic impedance from a laser activated molded interconnect device (MID) or a three-dimensional printer. The second matching layer being electrically coupled to the piezoelectric layer.

Optionally, the second matching layer is formed by the laser activated MID having a laser beam, such that a conductive layer of the second matching layer is formed by activating a bottom surface area of the second matching layer. Optionally, the material includes Acrylonitrile butadiene styrene (ABS), polycarbonate (PC), Polymerization (PA), Polyphthalamide (PPA), Polybutylene terephthalate (PBT), Cyclic Olefin Copolymer (COP), Polyphenyl Ether (PPE), Liquid-crystal polymer (LCP), Polyethylenimine (PEI), Polyether ether ketone (PEEK), or Polyphenylene sulfide (PPS). Optionally, the material includes a metallic particulate encapsulated with an organic coating such that the laser beam is configured to break down the organic coating to expose the metallic particles. The metallic particles are configured to attract a metal compound of a chemical electrolyte. Optionally, the second matching layer is formed by the 3D printer, the material representing a conductive material. Optionally, the 3D printer is configured to heat the conductive material using a laser based on the template. Optionally, the conductive material represents a metal powder or a metal wire.

It may be noted that the various embodiments may be implemented in hardware, software or a combination thereof. The various embodiments and/or components, for example, the modules, or components and controllers therein, also may he implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a solid-state drive, optical disk drive, and the like. The storage device may also be other similar means for loading computer programs or other instructions into the computer or processor.

As used herein, the term "computer," "subsystem," "controller circuit," "circuit," or "module" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of the term "controller circuit".

The computer, subsystem, controller circuit, circuit execute a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer, subsystem, controller circuit, and/o circuit to perform specific operations such as the methods and processes of the various embodiments. The set of instructions may be in the form of a software program. The software may be in various forms such as system software or application software and which may be embodied as a tangible and non-transitory computer readable medium. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein. Instead, the use of "configured to" as used herein denotes structural adaptations or characteristics, and denotes structural requirements of an structure, limitation, or element that is described as being "configured to" perform the task or operation. For example, a controller circuit, circuit, processor, or computer that is "configured to" perform a task or operation may be understood as being particularly structured to perform the task or operation having one or more programs or instructions stored thereon or used in conjunction therewith tailored or intended to perform the task or, operation and/or having an arrangement of processing circuitry tailored or intended to perform the task or operation). For the purposes of clarity and the avoidance of doubt, a general purpose computer (which may become "configured to" perform the task or operation if appropriately programmed) is not "configured to" perform a task or operation unless or until specifically programmed or structurally modified to perform the task or operation.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, they are by no means limiting and are merely exemplary. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f) unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or the examples include equivalent structural elements with insubstantial differences from the literal language of the claims.

What is claimed is:

1. An ultrasound probe comprising:
a piezoelectric layer; and
first and second matching layers, the first matching layer is interposed between the second matching layer and the piezoelectric layer, the second matching layer formed from a material having a select acoustic impedance, the material representing a laser activatable material, the second matching layer being electrically coupled to the piezoelectric layer, wherein the second matching layer is formed by the laser activatable material, such that a conductive layer of the second matching layer is formed by activating a bottom surface area of the second matching layer, wherein the laser activatable material includes a metallic particulate encapsulated with an organic coating that is laser activatable and breaks down to expose the metallic particulates, the metallic particles configured to attract a metal compound of a chemical electrolyte.

2. The ultrasound probe of claim 1, wherein the material includes Acrylonitrile butadiene styrene (ABS), polycarbonate (PC), Polymerization (PA), Polyphthalamide (PPA), Polybutylene terephthalate (PBT), Cyclic Olefin Copolymer (COP), Polyphenyl Ether (PPE), Liquid-crystal polymer (LCP), Polyethylenimine (PEI), Polyether ether ketone (PEEK), or Polyphenylene sulfide (PPS).

3. The ultrasound probe of claim 1, wherein the conductive material represents a metal powder or a metal wire.

4. The ultrasound probe of claim 1, wherein the second matching layer includes a conductive layer positioned along a backside of the second matching layer at an interface between the first and second matching layers, the conductive layer electrically coupled to ground.

5. An ultrasound probe comprising:
a piezoelectric layer; and
first and second matching layers, the first matching layer is interposed between the second matching layer and the piezoelectric layer, the second matching layer formed from a material having a select acoustic impedance, the material representing at least one of a laser activatable material or a three-dimensional (3D) printable material, the second matching layer being electrically coupled to the piezoelectric layer, wherein the conductive layer comprises a coating of metallic particulate encapsulated with an organic coating, the coating exposing the metallic particles on the backside of the second matching layer at the interface between the first and second matching layers.

6. The ultrasound probe of claim 1, wherein the material represents a laser activatable moldable material.

7. The ultrasound probe of claim 5, wherein the second matching layer is formed by the laser activated material, such that a conductive layer of the second matching layer is formed by activating a bottom surface area of the second matching layer.

8. The ultrasound probe of claim 5, wherein the material includes Acrylonitrile butadiene styrene (ABS), polycarbonate (PC), Polymerization (PA), Polyphthalamide (PPA), Polybutylene terephthalate (PBT), Cyclic Olefin Copolymer (COP), Polyphenyl Ether (PPE), Liquid-crystal polymer (LCP), Polyethylenimine (PEI), Polyether ether ketone (PEEK), or Polyphenylene sulfide (PPS).

9. The ultrasound probe of claim 5, wherein the organic coating is laser activatable such that the laser beam is configured to break down the organic coating to expose the metallic particles, the metallic particles are configured to attract a metal compound of a chemical electrolyte.

10. The ultrasound probe of claim 5, wherein the conductive material represents a metal powder or a metal wire.

11. The ultrasound probe of claim 5, wherein the second matching layer includes a conductive layer positioned along a backside of the second matching layer at an interface between the first and second matching layers, the conductive layer electrically coupled to ground.

* * * * *